United States Patent [19]

Berzin et al.

[11] Patent Number: 4,751,287

[45] Date of Patent: Jun. 14, 1988

[54] HUMAN LEUKOCYTE INTERFERON N AND A METHOD OF PRODUCING SAME IN BACTERIAL CELLS

[75] Inventors: Valdis M. Berzin; Alexandr J. Tsimanis; Jury I. Vishnevsky, all of Riga; Uldis R. Apsalon, Salaspils; Andris V. Dishler; Elmar Y. Gren, both of Riga; Evgeny D. Sverdlov, Moscow; Galina S. Monastyrskaya, Moscow; Sergei A. Tsarev, Moscow; Alexandr A. Smorodintsev; Vladimir I. Iovlev, both of Leningrad; Guna Y. Feldmane; Arnis E. Duk, both of Riga, all of U.S.S.R.

[73] Assignees: Institut Organicheskogo Sinteza Akademii Nauk Latviiskoi SSR, Riga; Institut Bioorganicheskoi Khimii Imeni M.M. Shemyakina akademii Nauk SSR, Leningrad, both of U.S.S.R.

[21] Appl. No.: 662,291

[22] PCT Filed: Feb. 23, 1984

[86] PCT No.: PCT/SU84/00007

§ 371 Date: Sep. 28, 1984

§ 102(e) Date: Sep. 28, 1984

[87] PCT Pub. No.: WO84/03300

PCT Pub. Date: Aug. 30, 1984

[51] Int. Cl.⁴ .................. C07K 13/00; C07K 15/26; A61K 45/02; C12P 21/00
[52] U.S. Cl. .................. 530/351; 424/85; 435/68; 435/811
[58] Field of Search .............. 424/85; 435/172.3, 68; 530/351

[56] References Cited

U.S. PATENT DOCUMENTS 4,414,150 11/1983 Goeddel .................. 424/85

FOREIGN PATENT DOCUMENTS 072541 2/1983 European Pat. Off. .
2079291 1/1982 United Kingdom .

OTHER PUBLICATIONS

Goeddel et al., Nature, vol. 290, pp. 20-26, 1981.
Nagata et al., J. Interferon Research, vol. 1, pp. 333-336, 1981.

*Primary Examiner*—Blondel Hazel
*Attorney, Agent, or Firm*—Burgess, Ryan & Wayne

[57] ABSTRACT

The human leukocyte interferon is essentially a protein featuring the following sequence of aminoacids:
CDLPQTHSLGNRRALILLAQMGRISHFSCLK-DRYDFGFPQEVFDGNQFQKAQAISAF HE-MIQQTFNLFSTKDSSAAWDETLLD-KFYIELFQQLNDLEACVTQEVGVEEIALMNE DSILAVRKYFQRITLYLMGKKYSPCAWEVV-RAEIMRSFSFSTNLQKGLRRKD.

A method for producing said interferon N is bacterial cells incorporates isolation of matrix poly (A)-mRNA from induced human leukocytes, synthesis of the gene of said interferon, insertion in the vector plasmid pBR 322 under the control of a tryptophane promotor, and transformation of the resultant recombinant DNA of the *E. coli* bacterial cells.

According to the invention, used as the interferon gene is the gene of interferon N featuring the following primary structure of DNA:

TGT GAT CTG CCT CAG ACT CAC AGC CTG GGT
AAT AGG AGG GCC TTG ATA CTC CTG GCA CAA
ATG GCA AGA ATC TCT CAT TTC TCC TGC CTG
AAG GAC AGA TAT GAT TTC GGA TTC CCC CAG
GAG CTG TTT GAT GGC AAC CAG TTC CAG AAG
GCT CAA GCC ATC TCT GCC TTC CAT GAG ATG
ATC CAG CAG ACC TTC AAT CTC TTC AGC ACA
AAG GAT TCA TCT GCT GCT TGG GAT GAG ACC
CTC CTA GAC AAA TTC TAC ATT GAA CTT TTC
CAG CAA CTG AAT GAC CTA GAA GCC TGT GTG
ACA CAG GAG GTT GGG GTG GAA GAG ATT GCC
CTG ATG AAT GAG GAC TCC ATC CTG GCT GTG
AGG AAA TAC TTT CAA AGA ATC ACT CTT TAT
CTG ATG GGG AAG AAA TAC AGC CCT TGT GCC
TGG GAG GTT GTC AGA GCA GAA ATC ATG AGA
TCC TTC TCT TTT TCA ACA AAC TTG CAA AAA
GGA TTA AGA AGG AAG GAT.

The human leukocyte interferon features an antiviral potency and can find application in medical practice.

1 Claim, No Drawings

HUMAN LEUKOCYTE INTERFERON N AND A METHOD OF PRODUCING SAME IN BACTERIAL CELLS

TECHNICAL FIELD

The present invention relates generally to genetic engineering and has particular reference to human leukocyte interferon N and a method for producing same in bacterial cells.

BACKGROUND ART

Interferons, and the leukocyte interferon inclusive, are essentially a class of inducible proteins in the vertebrates that are capable of exhibiting antiviral and antimicrobial activity, participating in regulation of immunological reactions of a cell and producing radioprotective and antitumorigenic effect. Human leukocyte interferons make up a multigene family incorporating not less than twelve members, which has been proved by an analysis of the structure of the chromosomal DNA and cDNA synthesized on the interferon mRNA, as well as by that of the aminoacid sequence of individual proteins from a heterogeneous mixture of human leukocyte interferons.

Known in the present state of the art are diverse human leukocyte interferons obtained by virtue of genetic engineering, e.g., interferon A produced by recombinan DNA in the cells of Escherichia coli (cf. Goeddel D. V. et al., Human leukocyte interferon produced by E. coli is biologically active, Nature, 1980, 287, 411–416), or human leukocyte interferon F (cf. Ovchinnikov Yu. A. et al., Direct expression of the gene of human leukocyte interferon F in the cells of E. coli, Transactions of the USSR Academy of Sciences, 1982, 265, 238–242 (in Russian), which is in effect a protein consisting of 166 aminoacids arranged in the following sequence:
CDLPQTHSLGNRRALILLAQM-
GRISPFSCLKDRHDFGFPQEEFDGNQF-
QKAQAISV LHEMIQQTFNLFSTKDSSAT-
WEQSLLEKFSTELNQQLNDMEACVIQEVG-
VEETPLM NVDSILAVKKYFQRITLYLTEK-
KYSPCAWEVVRAEIMRSFSLSKIFQERLRRKE A-ala; C-cys; D-asp; E-glu; F-phe; G-gly; H-his; l-ile; K-lys; L-leu; M-met; N-asn; P-pro; Q-gln; R-arg; S-ser; T-thr; V-val; W-trp; Y-tyr.

To produce the aforesaid interferon F the summary messenger RNA is produced from human blood leukocytes induced by Newcastle disease virus using the guanidine-chloride-guanidine-thiocyanate method. The poly-A fraction of mRNA is produced by double purification on oligo-dT-cellulose. The synthesis of cDNA is carried out using a synthetic oligonucleotide complementary to the gene of interferon within the sphere of translation termination. The synthesis of the second chain is performed with the aid of the Klenov's fragment of DNA-polymerase I. The thus-produced double-chain DNA is inserted after reconstruction, in the vector plasmid pBR 322 under the control of a tryptophane promotor. It is with the aforesaid recombinant plasmid that the E coli cells are transformed.

The aforementioned human leukocyte interferons differ from each other both in the efficacy of an inhibitory effect they produce on the cytopathic action of the same virus, and in the potency against most various viruses.

DISCLOSURE OF THE INVENTION

The invention is aimed at the provision of a novel human leukocyte interferon featuring the specificity of an antiviral and antiproliferative effect.

The human leukocyte interferon N of the invention is an essentially novel one and has not so far been described in literature.

The object of the invention is attained due to the fact that, according to the invention, the interferon N of the invention is in effect a protein featuring the following sequence of aminoacids:
CDLPQTHSLGNRRALILLAQMGRISHFSCLK-
DRYDFGFPQEVFDGNQFQKAQAISAF HE-
MIQQTFNLFSTKDSSAAWDETLLD-
KFYIELFQQLNDLEACVTQEVGVEEIALMNE
DSILAVRKYFQRITLYLMGKKYSPCAWEVV-
RAEIMRSFSFSTNLQKGLRRKD The novel human leukocyte interferon N disclosed in this invention features the specificity of both antiviral and antiproliferative effect. Practical application of this novel kind of interferon will make it possible to extend the range of medicines for producing a selective effect on viruses and malignant neoplasms.

A method of producing the aforementioned human leukocyte interferon N, consisting in isolation of matrix poly(A)-mRNA from induced human leukocytes, synthesis of the interferon gene, insertion in the vector plasmid pBR 322 under the control of a tryptophane promotor, and transformation of the thus-produced recombinant DNA of the E-coli bacterial cells, wherein, according to the invention, used as the interferon gene is the gene of interferon N featuring the following primary structure of DNA:

```
TGT GAT CTG CCT CAG ACT CAC AGC CTG GGT AAT AGG AGG GCC
TTG ATA CTC CTG GCA CAA ATG GCA AGA ATC TCT CAT TTC TCC
TGC CTG AAG GAC AGA TAT GAT TTC GGA TTC CCC CAG GAG GTG
TTT GAT GGC AAC CAG TTC CAG AAG GCT CAA GCC ATC TCT GCC
TTC CAT GAG ATG ATC CAG CAG ACC TTC AAT CTC TTC AGC ACA
AAG GAT TCA TCT GCT GCT TGG GAT GAG ACC CTC CTA GAC AAA
TTC TAC ATT GAA CTT TTC CAG CAA CTG AAT GAC CTA GAA GCC
TGT CTG ACA CAG GAG GTT GGG GTG GAA GAG ATT GCC CTG ATG
AAT GAG GAC TCC ATC CTG GCT GTG AGG AAA TAC TTT CAA ATA
ATC ACT CTT TAT CTG ATG GGG AAG AAA TAC AGC CCT TGT GCC
TGG GAG GTT GTC AGA GCA GAA ATC ATG AGA TCC TTC TCT TTT
TCA ACA AAC TTG CAA AAA GGA TTA AGA AGG AAG GAT.
```

BEST MODE OF CARRYING OUT THE INVENTION

To promote understanding of the present invention given below is a specific exemplary embodiment of a method for producing human leukocyte interferon N in bacterial cells.

EXAMPLE

1. Isolation, purification and characterization of poly-(A)-mRNA.

A total of $1.4 \cdot 10^{10}$ purified human blood leukocytes induced by Sendai virus (cf. Cantell K. et al., Meth. Enz, 1981, 78, part A, 29–38) are exposed to a 4.5-hour incubation, then are caused to precipitate by centrifugation within 30 min at 1500 rpm and are suspended in 100 ml of a 0.85-percent NaCl solution. The poly(A)-mRNA is isolated from the suspension of leukocytes and purified using the procedure described in literature (cf. Nagata S. et al., Nature, 1980, 284, 316–320) and incorporating affinity chromatography on oligo-dT-cellulose, fractionation in a linear gradient (5 to 20 percent) of saccharose and concentration of the 12s fraction on oligo-dT-cellulose. Assumed as the figure of merit of the poly(A)-mRNA is its matrix activity in the oocytes of *Xenopus laevis*, which is equal to 3000 AU of interferon per $\mu g$ of RNA with an average yield of 4 to 5 $\mu g$ of the 12s poly(A)-mRNA.

2. Synthesis of cDNA on the matrix of poly(A)-mRNA (a) Synthesis of single-chain cDNA The reaction mixture (600 $\mu l$) contains: 50 mM tris-HCl (pH=8.1), 6 mM $MgCl_2$, 5 mM dithiothreite, 150 mM KCl, a mixture of [$^3$H] dCTP, dATP, dTTP, dGTP-0.5 mM each, 7 $\mu g/ml$ poly(A)-mRNA, 20 $\mu g/ml$ oligo (dT)$_{12-18}$ and 200 AU/ml reverse transcriptase AMV. The reaction is carried out for one hour at 42° C. Upon termination of the synthesis added to the mixture is ethylenediaminetetraacetate (EDTA) till a concentration of 10 mM is obtained, the mixture is deproteinized with one volume of pheno and $CHCl_3$ (1:1), whereupon the aqueous medium is passed through a column (0.4·15 cm) packed with Sephadex G50 in 10 mM tris-HCl (pH=7.5), 0.25M NaCl. A complex of cDNA with poly(A)-mRNA is made to precipitate from the fractions with ethanol, and the precipitate is dissolved in 50 $\mu l$ $H_2O$. Then added to the solution is 5.1 $\mu l$ 5N NaOH solution, the latter is exposed to incubation within a 40-min period at 20° and then neutralized with 8.5 $\mu l$ 3M sodium acetate (pH=4.5) and doped with 30 $\mu l$ $H_2O$, whereupon the single-chain cDNA is precipitated with ethanol.

(b) Synthesis of double-chain cDNA

The precipitate of the single-chain cDNA is dissolved in 100 $\mu l$ of a reaction mixture (cf. Kurtz D. T. et al., Gene, 1981, 13, 145–152), containing 50 mM potassium-phosphate buffer solution (pH=7.4), mM $MgCl_2$, 1 mM 2-mercaptoethanol, a mixture of $\alpha$[-$^{32}$P]dTTP, dATP, dCTP, dGTP-50 $\mu M$ each, 100 AU/ml DNA-polymerase I (the Klenov's fragment), whereupon the reaction mixture is subjected to incubation for 30 minutes at 37° C. Upon termination of the reaction the product of the synthesis is isolated as described in Item 2 (a) above. After chromatography on Sephadex G50, the high-molecular fraction is rendered into solution (850 $\mu l$), containing 30 mM sodium acetate (pH=4.5), 03.M NaCl, 3 mM $ZnSO_4$, 2 $\mu g/ml$ tRNA of *E. coli* and 115 AU/ml nuclease $S_1$. The mixture is exposed to incubation for 30 minutes at 37° C., and the double-chain cDNA is isolated as described in Item 2 (a) above.

3. Cloning of vector plasmids pBR 322 in *E. coli* cells K-12 RRI, said plasmids carrying in the Pst L site the interferon gene built-in by the method of the oligo (dC)-oligo (dG) connectors (a) Attachment of connectors The oligo (dC) connectors are attached to the double-chain cDNA as follows.

An amount of 20 $\mu l$ of the reaction mixture contains 140 mM potassium cacodylate (pH=6.9), 4 $\mu M$ $ZnSO_4$, 0.8 mM 2-mercaptoethanol, 0.4 mM $CoCl_2$, 0.1 mM [$^3$H]d CTP, 100 mg double-chain cDNA and 50 AU/ml terminal deoxynucleotidyl-transferase. After 5-min incubation at 37° C. the reaction product is isolated using the procedure described in Item 2 (a) above.

The oligo (dG) connectors are attached to the plasmid pBR 322 split with restrictase Pst I in the following manner.

An amount of 125 $\mu l$ of the reaction mixture contains 200 mM potassium cacodylate (pH=6.9), 10 $\mu M$ $ZnSO_4$, 2 mM 2-mercaptoethanol, 4 mM $MgCl_2$, 1 mM $CoCl_2$, 0.2 mM $\alpha$[$^{32}$P]dCTP, 10 $\mu g$ plasmid pBR 322 split with restrictase Pst I, and 400 AU/ml terminal deoxynucleotidyl-transferase. The mixture undergoes incubation for 5 minutes at 37° C., and the product of the synthesis is isolated as described in Item 2 (a) above.

Under the aforestated reaction conditions 15 to 20 monomer units of dCMP and dCMP, respectively are attached to a molecule of the double-chain cDNA and the split plasmid pBR 322.

(b) Cloning of recombinant DNA in *E. coli* cells K.12 RRI

20 $\mu l$ of a solution of 6 ng cDNA and 40 ng vector obtained as described in Item 3 (a), in 10 mM tris-HCl (pH=7.5), 0.1M NaCl and 1 mM EDTA, is heated for 10 minutes at 65° C. and for two hours at 42° C., then cooled for 3 hours down to 22° C. and is employed for transformation, according to the method described in literature (cf. Dagert M. et al., Gene, 1979, 6, 23–28), of the *E. coli* cells K-12 RRI (F$^-$, pro, leu, thi, lac yl, str$^r$, $r_k{}^-$, $m_k{}^-$, endo I$^-$). It is in this way that 1200 tetracycline-resistant (5 $\mu g/ml$) transformants are obtained, of which 98 percent exhibit ampicillin-sensitivity (150 $\mu g/ml$) and are therefore applicable for the screening of recombinants.

4. Selection of recombinant DNA carrying the genes of human leukocyte interferon (a) Selection of recombinant DNA carrying the genes of human leukocyte interferon is carried out with the aid of [$^{32}$P] tracer-isotope labelled sixteen-member synthetic oligonucleotide sondes featuring the respective sequences of aminoacids: dTCTCATCATTTCTCCT (A) and dCCTCTCATCTCCCTCA (B), complementary to the conservative portions of nucleotides 504–519 of the coding chain and of nucleotides 68–83 of the noncoding chain, respectively, which are most characteristic of a majority of the presently known genes of human leukocyte interferon (cf. Goeddel D. V. et al., Nature, 1981, 290, 20–26). To insert a 5' terminal marker, 30 mmole oligonucleotide is incubated for 30 minutes at 37° C. in 20 $\mu l$ of the reaction mixture, containing 50 mM tris-HCl (pH=8.0), 5 mM dithiothreite, 7 mM $MgCl_2$, 3 $\mu M$ $\gamma_1$-[$^{32}$P] ATP and 20 AU of the bacteriophage T4 polynucleotidekinase. The 5'-[$^{32}$P]-labelled oligonucleotide is purified by virtue of chromatography on Sephadex G50 (0.4.22 cm) in $H_2O$.

(b) Hybridization of colonies on nitrocellulose filters with the 5'-[$^{32}$P]-labelled oligonucleotide sondes The $T_c{}^r A_p{}^s$ transformants are grown on nitrocellulose filters (90 mm in diameter) until colonies appear, whereupon the filters are transferred to agar doped with chloroamphenicol (500 $\mu g/ml$), and incubation continues for 18 hours. Further on the filters are treated with 0.5N NaOH, followed by neutralization in 1M tris-HCl (pH=8.0) and vacuum drying (2 to 4 hours at 80°); next the filters are subjected to prehybridization for 2 hours at 37° C. in a mixture of 0.15M tris-HCl (pH=8.0), 0.75M NaCl, 5 mM EDTA, 1 mM Na$_2$HPO$_4$, 250 µg/ml tRNA and sodium dodecylsulphate, bovine serum albumine (BSA), phycol and polyvinylpyrrolidone-0.1 percent each. After drying on a filter paper, the filters are wetted with the aforementioned mixture (300 µl/filter), containing 1·10$^6$ imp/min/ml of the 5'-[$^{32}$P]-oligonucleotide, are sealed in a polyethylene bag and incubated for 20 hours at 37°. After hybridization the filters are washed out three times in succession at 22° C. with 0.1M tris-HCl solution (pH=8.0), 0.5M NaCl solution and 0.1-percent sodium dodecylsulphate solution, then are subjected to drying and X-ray autographing for 20 to 70 hours. Autoradiography of the filters has revealed a few colonies positive to hybridization with the both of the 5'-[$^{32}$P]-labelled oligonucleotide sondes A and B. A restriction analysis of the plasmid DNA from these colonies and an analysis of the nucleotide sequence of the inserted cDNA have demonstrated that one recombinant DNA pIFN 105 contains a short sequence of the 5'-nontranslatable segment, a coding sequence of a complete gene of human leukocyte interferon and of a novel kind of leukocyte interferon N, and 370 nucleotides 3 of the nontranslatable gene segment.

5. Constructing recombinant DNA capable of synthesizing interferon N in *E. coli* cells (a) Plasmid pIFN 105-I carrying the gene of interferon N under the control of t$_{rp}$ promotor. The DNA of the recombinant plasmid pIFN 105, containing the aforementioned gene of interferon N, is isolated from the lysate of transformed *E. coli* cells and is purified on hydroxyapatite according to the presently known procedure (cf. Colman A. et al., J. Biochem., 1978, 91, 303–310). Then 50 µg DNA is treated with restrictase PsTI, and the cleavage products are electrophoretically separated in a 0.8-percent agarose gel. The fragment of DNA (containing some 960 pairs of bases) and incorporating the interferon gene, is isolated by virtue of electroelution and purified as described in literature (cf. Analyt. Biochem., 1981, 112, 295–298). Next 10 µg of the DNA fragment is split with restrictase BamH I, the mixture is treated with nuclease S$_I$ (0.5 AU/µg DNA) for 30 minutes at- 22°, whereupon a great BamH I-Pst fragment (947 pairs of bases), after having been subjected to electrophoresis in a 1.5-percent agarose gel is isolated in a way similar to that described with reference to the PstI fragment.

A quantity of 5 µg of the pBR 322-trp vector plasmid (cf. Ovchinnikov Yu. A. et al., Transactions of the USSR Academy of Sciences, 1982, 265, 238–242 (in Russian), containing the promotor segment of the tryptophane operon of *E. coli*, is subjected to splitting with restrictase RI of *E. coli*, the adhesive ends of DNA are filled with polymerase I (the Klenov's fragment) according to the procedure described in literature (cf. Backman K. et al., Proc. Nat. Acad. Sci. USA, 1976, 73, 4171–4178), 1.5 µg vector is subjected to doping for 18 hours at 10° C. in 10 µl of a buffer solution of 50 mM tris-HCl (pH=7.6), 10 mM MgCl$_2$, 10 mM dithiothreite containing 0.27 µg of a DNA fragment with the interferon gene, and 20 AU of the T$_4$ DNA-ligase. The mixture is diluted with 150 µl of the buffer solution of 10 mM tris-HCl (pH=7.5), 50 mM NaCl, 1 mM EDTA, and the *E. coli* cells K-12 RRI are transformed. Then the transformants containing the interferon gene are selected by hybridization of colonies as described in Item 4 (b). It is by virtue of a restriction analysis that the plasmid pIFN 105-I has been identified, containing the gene of preinterferon N under the control of a tryptophane promotor.

Thereupon the *E. coli* cells K-12RRI transformed with the plasmid pIFN 105-I, are grown on a culture medium containing (g/l): bacto-tryptone-10.0; yeast extract-5.0; NaCl-10.0; ampicillin-0.02; till an optical density of A$_{650}$=1.0 is obtained, whereupon they are caused to precipitate and are destructed by treatment with lysozyme and subjecting to repeated freezing-thawing cycles as described in literature (cf. Nature, 1980, 284, 316–320).

The interferon activity is within 0.5 to 1.0·10$^6$ AU per liter of a bacterial suspension.

(b) Expression plasmid of mature interferon N

A quantity of 5 µg of a great BamHI-Pst I fragment (DNA pIFN 105) is subjected to partial hydrolysis with restrictase Sau 3A (2 AU/µg DNA for 5 minutes at 37° C.), then a mixture of the fragments is separated by virtue of electrophoresis in a 1.5-percent agarose gel, whereupon a fragment comprising 869 nucleotides is isolated, which contains the gene of maturated interferon less the first codon. Then added to said fragment with its adhesive ends is a synthetic nucleotide (cf. Transactions of the USSR Academy of Sciences, 1982, 265, 238–242 (in Russian) containing Eco RI and Sau 3A, and the fragment is subjected to ligation with respect to the Pst I and Eco RI sites of the vector plasmid pBR 322. Next the *E. coli* cells are transformed with recombinant DNA and, after hybridization with the sondes and restriction analysis of DNA, the plasmid pIFN18 is selected from the transformants, said plasmid carrying the modified gene of mature interferon N. Then the short fragment Eco RI-Pst I of the plasmid pIFN18 containing the modified gene of interferon is subjected to ligation with the Pvu II-Eco Ri-carrying fragment (340 pairs of bases) of DNA plasmid pBR 322-trp, carrying the trp-promotor, and 0.4 µg of the end product is inserted in the Pst I and the EcoR I-filled site of the vector plasmid pBR 322. Upon transformation of the *E. coli* cells RRI, there are selected 1000 Tc$^r$Ap$^s$ clones, the recombinant DNA are then exposed to hybridization and restriction analysis, and the plasmid pIFN 18-38 is selected, containing the gene of mature interferon N under the control of a tryptophane promotor.

The yield of leukocyte interferon N ranges between 4 and 6.10$^8$ AU per liter of the bacterial suspension.

Industrial Applicability

The human leukocyte interferon N as proposed in the present invention features an antiviral potency and can find application in medical practice as an antiviral, antimicrobial and antineoplastic drug.

What is claimed is:

1. A human leukocyte interferon N, which is in effect a protein featuring the following sequence of aminoacids:
CDLPQTHSLGNRRALILLAQM-
GRISHFSCLKDRYDFGFPQEVFDGNQF-
QKAQAISAF HEMIQQTFNLFSTKDSSAAW-
DETLLDKFYIELFQQLNDLEACVTQEVG-
VEEIALMNE DSILAVRKYFQRITLYLMG-
KKYSPCAWEVVRA-
EIMRSFSFSTNLQKGLRRKD.

* * * * *